United States Patent [19]
McKinnie

[11] Patent Number: 5,847,232
[45] Date of Patent: Dec. 8, 1998

[54] PROCESS FOR THE PREPARATION OF TETRABROMOBISPHENOL-A

[75] Inventor: Bonnie G. McKinnie, Magnolia, Ark.

[73] Assignee: Albemarle Corporation, Richmond, Va.

[21] Appl. No.: 884,420

[22] Filed: Jun. 27, 1997

Related U.S. Application Data

[63] Continuation of Ser. No. 426,998, Apr. 24, 1995, abandoned, which is a continuation-in-part of Ser. No. 398,837, Mar. 6, 1995, abandoned.

[51] Int. Cl.$^6$ ............................................. C07C 39/16
[52] U.S. Cl. ............................................. 568/726
[58] Field of Search .................. 568/721, 722, 568/726, 727, 723, 776, 779

[56] References Cited

U.S. PATENT DOCUMENTS

| | | | |
|---|---|---|---|
| 2,455,652 | 12/1948 | Bralley et al. | 260/77.5 |
| 3,029,291 | 4/1962 | Dietzler | 260/619 |
| 3,143,575 | 8/1964 | Bryner et al. | 260/619 |
| 3,182,088 | 5/1965 | Hennis | 260/619 |
| 3,234,289 | 2/1966 | Hennis | 260/619 |
| 3,363,007 | 1/1968 | Majewski et al. | 260/619 |
| 3,546,302 | 12/1970 | Asadorian et al. | 260/619 |
| 3,868,423 | 2/1975 | Montanari et al. | 260/619 A |
| 3,929,907 | 12/1975 | Janzon et al. | 260/619 R |
| 4,013,728 | 3/1977 | Brackenridge | 260/619 A |
| 4,036,894 | 7/1977 | Jenkner | 260/619 A |
| 4,112,242 | 9/1978 | Swietoslawski et al. | 568/726 |
| 4,180,684 | 12/1979 | Kleinschmit et al. | 568/726 |
| 4,282,391 | 8/1981 | Quinn et al. | 568/726 |
| 4,283,566 | 8/1981 | Mark | 568/726 |
| 4,291,177 | 9/1981 | Mark et al. | 568/726 |
| 4,302,614 | 11/1981 | Dannenberg et al. | 568/641 |
| 4,451,675 | 5/1984 | Bounds | 568/726 |
| 4,628,124 | 12/1986 | McKinnie et al. | 568/726 |
| 4,692,555 | 9/1987 | Shin | 568/722 |
| 4,701,568 | 10/1987 | Mckinnie et al. | 568/726 |
| 4,783,556 | 11/1988 | Mitchell et al. | 568/726 |
| 4,909,997 | 3/1990 | Mitchell et al. | 422/225 |
| 4,990,321 | 2/1991 | Sato et al. | 423/486 |
| 5,008,469 | 4/1991 | Eguchi et al. | 568/722 |
| 5,017,728 | 5/1991 | McKinnie et al. | 568/726 |
| 5,059,722 | 10/1991 | Mitchell et al. | 568/226 |
| 5,059,726 | 10/1991 | Eguchi et al. | 568/726 |
| 5,068,463 | 11/1991 | Walter | 568/726 |
| 5,107,035 | 4/1992 | Hines et al. | 568/726 |
| 5,138,103 | 8/1992 | Eguchi et al. | 568/726 |
| 5,208,389 | 5/1993 | McKinnie et al. | 568/726 |
| 5,237,112 | 8/1993 | LaRose | 568/726 |
| 5,283,375 | 2/1994 | McKinnie et al. | 568/726 |
| 5,302,761 | 4/1994 | Tamabayashi et al. | 568/726 |
| 5,446,212 | 8/1995 | Sanders et al. | 568/726 |

FOREIGN PATENT DOCUMENTS

| | | |
|---|---|---|
| 686772 | 5/1964 | Canada ............... 260/620 |
| 706433 | 3/1965 | Canada ............... 260/620 |
| 0367869 | 5/1990 | European Pat. Off. . |
| 0380363 | 8/1990 | European Pat. Off. . |
| 0380365 | 8/1990 | European Pat. Off. . |
| 0472395 | 2/1992 | European Pat. Off. . |
| 0572154 | 12/1993 | European Pat. Off. . |
| 0574031 | 12/1993 | European Pat. Off. . |
| 2274586 | 1/1976 | France . |
| 2041220 | 3/1971 | Germany . |
| 3417027 | 11/1985 | Germany . |
| 64410 | 11/1981 | Israel . |
| 225034 | 12/1983 | Japan . |
| 58728 | 12/1985 | Japan . |
| 48641 | 3/1987 | Japan . |
| 316748 | 12/1988 | Japan . |
| 196747 | 8/1990 | Japan . |
| 4-099743 | 3/1992 | Japan . |
| 5-213804 | 8/1993 | Japan . |
| 5-229976 | 9/1993 | Japan . |
| 379054 | 12/1993 | Japan . |
| 2026280 | 1/1995 | U.S.S.R. . |
| 949306 | 2/1964 | United Kingdom . |
| 1031500 | 6/1966 | United Kingdom . |
| 1316415 | 5/1973 | United Kingdom . |
| 9620911 | 7/1996 | WIPO . |

OTHER PUBLICATIONS

Levenspiel Chemical Reaction Eng. (1962) p. 126, 1962.
Sadygov, et al., "Oxidative bromination of 2,2–bis(4'–hydroxyphenyl)propane," Institute of Organochlorine Synthesis, Academy of Sciences of the Azerbaidzhan SSR, Sumgait, U.S.S.R., 1990, pp. 109–112 (Translation attached—pp. 1–7.
Chemical Abstract No. 104(17):148492y–*Chemical Abstracts*, vol. 104, 1986, p. 656.
Chemical Abstract No. 104(23):206899z–*Chemical Abstracts*, vol. 104, 1986, p. 716.
Islam et al., "Tetrahalogenated 4:4'–Dihydroxydiphen;ylalkanes, their Synthesis and some of their Reactions," *Egypt. J. Chem.* 20, No. 5, pp. 483–490 (1977).
Chemical Abstract No. 78(1):3946j–*Chemical Abstracts*, vol. 78, 1973, p. 328.
Chemical Abstract No. 86(25):189500c–*Chemical Abstracts*, vol. 86, 1977, p. 570.
Chemical Abstract No. 96(19):162322r–*Chemical Abstracts*, vol. 96, 1982, p. 718.
Patent Abstract of Japan–Publication No. JP620486641, Publication Date Mar. 3, 1987, entitled "Bromination of Bisphenol Compound".

*Primary Examiner*—Alan Siegel
*Attorney, Agent, or Firm*—E. E. Spielman, Jr.

[57] ABSTRACT

This invention relates to a process for the production of tetrabromobisphenol-A, which process features: a water and water miscible solvent reaction medium; a relatively high reaction temperature; and the presence, in the reaction medium, of unreacted $Br_2$ during the feed of bisphenol-A to the reactor.

30 Claims, No Drawings

2

PROCESS FOR THE PREPARATION OF TETRABROMOBISPHENOL-A

CROSS-REFERENCE TO RELATED APPLICATION

This application continuation of Ser. No. 08/426,998, filed Apr. 24, 1998, now abandoned which is a continuation-in-part of Ser. No. 08/398,837, filed Mar. 6, 1995 now abandoned.

BACKGROUND OF THE INVENTION

This invention relates to highly efficient processes for the preparation of tetrabromobisphenol-A.

Tetrabromobisphenol-A is one of the most widely used brominated flame retardants in the world. It is used extensively to provide flame retardency for styrenic thermoplastics and for some thermoset resins.

The commercial processes used to produce tetrabromobisphenol-A generally fall into three categories. The first category includes those processes in which substantial amounts of methyl bromide are co-produced along with the tetrabromobisphenol-A. Generally, up to 40–50 pounds of methyl bromide can be expected per 100 pounds of tetrabromobisphenol-A produced. The methyl bromide co-production is now considered desirable since there is a substantial market for this bromide as a fumigant and as a pharmaceutical or agricultural chemical intermediate. In most cases, the processes within this first category feature reacting bisphenol-A and bromine in methanol. The ar-bromination of the bisphenol-A is a substitution reaction which generates one mole of HBr per ar-bromination site. Thus, for the production of tetrabromobisphenol-A, four moles of HBr are generated per mole of tetrabromobisphenol-A produced. The HBr in turn reacts with the methanol solvent to produce the methyl bromide co-product. After the bisphenol-A and bromine feed are finished, the reactor contents are cooked for one to two hours to complete the reaction. At the end of the reaction, water is added to the reactor contents to precipitate out the desired tetrabromobisphenol-A product.

The second category of processes features the production of tetrabromobisphenol-A without the co-production of substantial amounts of methyl bromide and without the use of oxidants to convert the HBr to $Br_2$. See U.S. Pat. No. 4,990,321; U.S. Pat. No. 5,008,469; U.S. Pat. No. 5,059,726; and U.S. Pat. No. 5,138,103. Generally, these processes brominate the bisphenol-A at a low temperature, say 0° to 20° C., in the presence of a methanol solvent and a specified amount of water. The water and low temperature attenuate the production of methyl bromide by slowing the reaction between methanol and HBr. The amount of water used, however, is not so large as to cause the precipitation of the tetrabromobisphenol-A from the reaction mass. Additional water for that purpose is added at the end of the reaction. One drawback with this type of process is that it uses a fairly long aging or cook period after the reactants have all been fed and it requires additional process time for the final precipitation of tetrabromobisphenol-A via the last water addition.

In the third category are those processes which feature the bromination of bisphenol-A with bromine in the presence of a solvent and, optionally, an oxidant, e.g., $H_2O_2$, $Cl_2$, etc. See U.S. Pat. No. 3,929,907; U.S. Pat. No. 4,180,684; U.S. Pat. No. 5,068,463 and Japanese 77034620 B4 77/09/05. The solvent is generally a water immiscible halogenated organic compound. Water is used in the reaction mass to provide a two-phase system. As the bisphenol-A is brominated, the tetrabromobisphenol-A is found in the solvent. The co-produced HBr is present in the water. When used, the oxidant oxidizes the HBr to $Br_2$, which in turn is then available to brominate more bisphenol-A and its underbrominated species. By oxidizing the HBr to $Br_2$, only about two moles of $Br_2$ feed are needed per mole of bisphenol-A fed to the reactor. To recover the tetrabromobisphenol-A from the solvent, the solution is cooled until tetrabromobisphenol-A precipitation occurs. This process type is not a panacea though, as there is the expense of handling, purifying and recycling the halogenated organic solvent. In addition, the cooling of the solution to recover tetrabromobisphenol-A entails additional expense and process time.

As long as there is a viable market for methyl bromide, the processes of the first category have been found to be commercially attractive. However, it is now being proposed, on an international level, that the use of methyl bromide as a fumigant be prohibited. Since the fumigant market is the main market for methyl bromide, a need is apparent for tetrabromobisphenol-A processes which do not co-produce a substantial amount of methyl bromide. This is a difficult task since such processes, to be commercially successful, will be required to economically produce tetrabromobisphenol-A without the benefit of the revenue realized from the sale of the co-produced methyl bromide.

THE INVENTION

The processes of this invention feature the efficient production of high-quality tetrabromobisphenol-A in high yields. The processes can be run in the batch mode or in the continuous mode. When run in the batch mode, process efficiency is enhanced due to relatively short reactor times as there is no need for a time consuming one hour plus post-reaction cook period or a post-reaction tetrabromobisphenol-A precipitation step. The use of a continuous process for the production of tetrabromobisphenol-A is unique in itself and is made possible by the short reaction and tetrabromobisphenol-A precipitation times which are features of the processes of this invention. In the continuous mode, reactor size can be substantially reduced without a loss in product output.

In addition to the above reaction efficiencies, the processes of this invention are capable of producing high yields of tetrabromobisphenol-A in a methanol based solvent without the substantial concomitant production of methyl bromide, say as low as 1.0 to 0.2 lbs of methyl bromide per 100 lbs of tetrabromobisphenol-A product. Even further, it is possible to obtain high yields of tetrabromobisphenol-A even though only about 2 moles of $Br_2$ per mole of bisphenol-A are fed to the reactor.

It has been discovered that the foregoing benefits can be obtained by (1) brominating bisphenol-A in the presence of a water miscible solvent, e.g., methanol, and a relatively large amount of water while maintaining the reaction mass at a relatively high temperature and, optionally, concurrent therewith, (2) oxidizing HBr produced in the reaction mass to $Br_2$ for use in the bromination. As will be discussed later, the features in (1) have conventionally been considered conducive to the low-yield production of low-quality tetrabromobisphenol-A and/or the co-production of methyl bromide.

In accordance with this invention, tetrabromobisphenol-A can be produced by:

a. feeding, to a reactor, a solution comprised of bisphenol-A, water and a water miscible solvent to at least partially form a reaction mass having a liquid phase containing from above about 15 to about 65 wt % water, the wt % being based upon the amount of water and water miscible solvent in the liquid phase;

b. during (a), providing for the presence of unreacted $Br_2$ in the reaction mass to yield a tetrabromobisphenol-A precipitate; and c. having a reaction mass temperature which is within the range of from about 30° to about 100° C.

Also, in accordance with this invention, tetrabromobisphenol-A can be produced by:

a. co-feeding, to a reactor, $Br_2$ and a solution comprised of bisphenol-A, water and a water miscible solvent to at least partially form a reaction mass having a liquid phase containing from above about 15 to about 65 wt % water, the wt % being based upon the amount of water and water miscible solvent in the liquid phase;

b. during (a), the liquid phase containing at least about 50 ppm unreacted $Br_2$; and c. having a reaction mass temperature within the range of from about 30° to about 100° C.

The formation of the reaction mass can best be accomplished by co-feeding the $Br_2$ and bisphenol-A/water/solvent solution. By co-feeding, it is meant that the $Br_2$ and solution feed periods overlap one another to at least some extent. (A feed period is that period of time over which all of a subject feed is fed to the reactor.) For example, the $Br_2$ feed can be initiated and then followed by the solution feed, with both feeds thereafter occurring simultaneously until finished. Another example would be that of an initial $Br_2$ feed followed by a continuous solution feed which is accompanied by a continued, but intermittently interrupted or staged, $Br_2$ feed. Yet another example is that of initiating the $Br_2$ feed followed by the solution feed so that the two feeds occur simultaneously until the specified amount of $Br_2$ has been fed. At that point, the solution feed continues alone until it is finished. Other co-feed schemes could feature an intermittently interrupted solution feed, or initially feeding the solution into a $Br_2$ containing reactor followed by a combined $Br_2$ and solution feed. Finally, the $Br_2$ and solution feeds can be, timewise, completely concurrent one with the other.

Feeds that do not have some overlap of the $Br_2$ and solution feed periods are possible, but will not be generally preferred. For example, all of the $Br_2$ can be fed followed by the solution feed. However, depending on reaction conditions, such a feed scheme could lead to the formation of undesirable by-products due to the high concentration of $Br_2$ which is seen by the initial bisphenol-A feed. Another scheme, i.e., feeding large amounts of bisphenol-A before feeding $Br_2$, would not be preferred as it could lead to precipitation of substantial amounts of tribromobisphenol-A.

However the feeding occurs, it must be in harmony with the requirements of step (b) of the process.

Commercially available $Br_2$ is suitable for use as the $Br_2$ feed. Should the $Br_2$ contain undesirable impurities, it can be treated by conventional purification techniques, e.g., distillation, $H_2SO_4$ treatment, etc., which are well known to those skilled in the art.

The $Br_2$ can be fed as a liquid or as a gas to the reactor. It is preferred that the feed be gaseous. Whether the $Br_2$ is liquid or gaseous, it is preferred that the feed entry point be sub-surface of the reaction mass. This is conveniently accomplished by use of a dip tube. If the feed is liquid, above-surface feed must contend with possible splattering and inefficient mixing.

The amount of water in the reaction mass should be within the range of from above about 15 to about 65 wt % water based upon the total amount of water and water miscible solvent in the liquid phase of the reaction mass. Preferably, the amount of water fed is that amount which is within the range of from about 25 to about 65 wt % water. Most highly preferred is the range of from about 25 to about 50 wt %. When the water miscible solvent is methanol, the preferred amount of water is from about 30 to about 45 wt %.

The water content of the reaction mass is an important aspect of this invention. It is believed, though the processes of this invention are not to be limited by any particular theory, that the water content greatly attenuates the formation of methyl bromide and, at the same time, allows for a high-purity tetrabromobisphenol-A product.

The formation of methyl bromide is attenuated because HBr, which is co-produced by the substitution bromination reaction between bisphenol-A and $Br_2$, is diluted by the large amount of water in the reaction mass. Further, the HBr reacts with the water to yield $H_3OBr$ which is very slow to react with a water miscible solvent, e.g., methanol.

In view of the amount of water present, the tetrabromobisphenol-A product purity is unexpected. Normally, it would be expected that this amount of water would cause under-brominated species, e.g., tribromobisphenol-A, to precipitate along with the tetrabromobisphenol-A species. This co-precipitation would be contrary to the obtainment of a highly pure tetrabrominated product. Not only does the large amount of water not act detrimentally towards the processes of this invention, but actually, instead, it benefits the tetrabromination reaction. Without being limited to any particular theory, it is believed that the water enhances the presence of brominating species in the reaction mass. With this enhancement, there is a favoring of the bromination of the bisphenol-A all of the way to tetrabromobisphenol-A before the intermediate tribromobisphenol-A has sufficient opportunity to form a precipitate. It is believed that the enhancement of the brominating species is due to the fact that HBr reacts with water to form the $H_3OBr$ acid. The $H_3OBr$ acid does not react with $Br_2$. This is important because if $H_3OBr$ was not formed, a larger quantity of HBr would be available to react with $Br_2$ to form $HBr_3$ The formation of $HBr_3$ is not desired as it is a non-brominating species in the reaction mass. Thus, the formation of $HBr_3$ consumes reaction mass $Br_2$ which in turn results in a slowing of the bromination reaction. This slowing of the bromination reaction can result in an increase in the precipitation of tribromobisphenol-A.

The water content is not the only factor affecting the quantity of HBr in the reaction mass. The HBr quantity can also be reduced by reacting the HBr with an oxidant in accordance with this invention. As will be discussed later, the optional use of an oxidant will convert at least some of the HBr to $Br_2$. Thus, the large amount of water and the use of an oxidant can both contribute to enhancing the presence of brominating species in the reaction mass.

The water being fed to the reactor has heretofore been described as being part of a solution which also contains bisphenol-A and a water miscible solvent. Feeding the water as part of such a solution is convenient and preferred. However, the water may be introduced into the reaction mass in other equivalent ways. For example, the water can be fed as a separate feed stream. Such a feed could be essentially contemporaneous with the feed of a solution of bisphenol-A and water miscible solvent. Even further, a portion, if not all, of the water can be fed as steam or steam condensate along with a gaseous $Br_2$ feed. The steam could have been used to vaporize the $Br_2$ to form the gaseous feed. Another example features providing water as a charge or as part of a charge to the reactor prior to initiating the feeds and adjusting the amount of water later fed to obtain the desired water content in the reaction mass. However, the water is provided to the reaction mass, the only requirement for the water feed is that it be such that the proper amount of water be present in the reaction mass during substantially all of the reaction period.

In those cases where the amount of water used is in the lower end of the range, say 15 to 25 wt %, it may be desirable to add some additional water at the end of the bisphenol-A bromination. The possible advantage to such an addition is that the additional water may cause further precipitation of tetrabromobisphenol-A from the reaction mass. The further precipitation goes towards increasing the yield of the process. In these cases, the added water is counted in the total solution water.

The feed of the water miscible solvent has been described above in conjunction with the feed of the solution. However, the solvent feed need not always be exclusively as a constituent of the solution provided that the solvent's functions are not hindered. For example, a portion of the solvent can be fed as part of the solution as is needed to solvate the bisphenol-A in the solution, while the remaining portion, generally a smaller portion, can be fed as a separate stream. From a practical standpoint though, the solvent is best fed as a solution constituent.

As can be appreciated from the foregoing, the manner in which the water, solvent and/or solution can be fed is not critical to the processes of this invention provided that the reaction mass is properly constituted. Thus, to simplify matters for discussion, the feed of the solution, which comprises bis-phenol-A, water and water miscible solvent, is to mean that the water can be fed as a constituent of the solution, as a separate stream or as a combination of both and that the solvent can all be fed as a constituent of the solution or as a portion in the solution and as a portion in a separate stream. Also to be considered as part of the solution feed is any water or solvent which is provided to the reaction mass as a pre-feed charge or as, a part of such a charge to the reactor.

The water miscible solvent can be defined functionally as a material which is capable of solvating $Br_2$, bisphenol-A, monobromobisphenol-A, dibromobisphenol-A and tribromobisphenol-A under reaction conditions. The reaction conditions of special import are the reaction mass temperature, the presence of unreacted $Br_2$ in the reaction mass and the reaction mass water content. Further, the solvent should be substantially inert with regard to $H_3OBr$ and the ar-bromination of the bisphenol-A to tetrabromobisphenol-A and not contribute to the production of troublesome amounts of color bodies, ionic bromides and/or hydrolyzable bromides. Hydrolyzable bromides include 1-bromo-2-methoxy-2-(3',5'-dibromo-4'-hydroxyphenyl)propane, 1,1-dibromo-2-methoxy-2-(3',5'-dibromo-4'-hydroxyphenyl)propane, 1,3-dibromo-2-methoxy-2-(3',5'-dibromo-4'-hydroxyphenyl)propane, and 1,1,3-tribromo-2-methoxy-2-(3',5'-dibromo-4'-hydroxyphenyl)propane. The solvent, when taken in combination with the water and reaction conditions of the processes of this invention, can have some small ability to solvate tetrabromobisphenol-A, but for the sake of reaction yield, the solvating power should be low, say no more than about 20 wt % and preferably no more than about 5 wt % solvated tetrabromobisphenol-A in the liquid phase of the reaction mass.

Exemplary of the preferred water miscible solvents are water miscible alcohols, carboxylic acids, e.g., acetic acid, and nitrites, e.g., acetonitrile. Some ethers may also be suitable provided they are not cleaved by the acidic nature of the reaction mass. The more preferred solvents are the alcohols having up to 4 carbon atoms. Most preferred are ethanol and methanol, with methanol being the solvent of choice. Methanol is relatively inexpensive and is easily recovered by simple distillation techniques for recycle. Since there is a large water presence ink the processes of this invention, it is not necessary to recover the methanol with a low water content, thereby reducing the methanol recovery cost.

When methanol is not used as the water miscible solvent, the co-production of methyl bromide is obviously not of concern. However, if the product between the HBr and the solvent is not a commercially desirable product, its production is not wanted. Thus, the features of the process of this invention are beneficial whether or not the solvent is methanol.

The amount of water miscible solvent used is best related to the amount of bisphenol-A fed and can be conveniently expressed as the weight ratio of the solvent to bisphenol-A. Preferably, the ratio is within the range of from about 2:1 to about 10:1, and most preferably within the range of from about 3:1 to about 5:1. More or less solvent can be used, provided that the solvent function mentioned above is accomplished.

The $Br_2$ and solution feed streams are preferably at a temperature which promotes process efficiency in view of the desired reaction mass temperature. A suitable liquid $Br_2$ feed temperature is from about 10° C. to just below the boiling point of $Br_2$. If the $Br_2$ is to be fed as a gas, then the $Br_2$ stream temperature should be that which is conducive to such a feed. For example, such a feed temperature may be within the range of from about 60° to about 100° C. The solution feed temperature should be that which does not detrimentally cool or heat the reaction mass or which requires pressure operation so that the feed can be made in the liquid state. If the solution feed is to be made with separate water and/or solvent feeds, then the same comments made above with regard to temperature apply to the separate feeds.

The $Br_2$ and solution and/or separate water, etc., feeds all contribute to the formation of the reaction mass in the reactor. These feeds will produce a reaction mass liquid phase (liquid portion) and, because of the formation of tetrabromobisphenol-A precipitate, ultimately a reaction mass solid phase (solid portion). At least a portion of the $Br_2$ feed, be it fed as a gas or as a liquid, will be consumed in the bromination reaction. Any non-consumed $Br_2$ feed will be found in the liquid phase and be joined there by any non-consumed $Br_2$ produced by the optional oxidation of HBr present in the reaction mass. While the identity of the source of the unreacted $Br_2$ in the liquid phase is lost, the combination of non-consumed $Br_2$ from the feed and from the oxidized HBr provides for the excess of unreacted $Br_2$ in the liquid phase which is a feature of this invention.

The unreacted $Br_2$ in the liquid phase of the reaction mass is extant as the solution is being fed. It is permissible for the unreacted $Br_2$ content in the reaction mass to disappear for brief periods of time depending on the level of under-brominated species that can be tolerated in the tetrabromobisphenol-A reaction product and/or upon the extent of precipitation of the under-brominated species which is realized. In fact, if the period of time is real brief and favorable reaction parameters are chosen, the formation of these under-brominated precipitates may not occur to any appreciable extent at all. The practitioner will have to observe the process and determine by empirical methods the sensitivity of the chosen reaction conditions to the brief absence of unreacted $Br_2$ in the reaction mass. Thus, for the purposes of this invention the "presence of unreacted $Br_2$" encompasses brief periods of time in which the unreacted $Br_2$ content can be nil, but which does not result in the formation of under-brominated species to an extent that results in an unacceptable tetrabromobisphenol-A product, say one containing less that about 96 wt % tetrabromobisphenol-A.

Quantifying the preferred amount of unreacted $Br_2$ in the reaction mass liquid phase is best handled by a trial and error technique. A trial process is first defined by choosing an unreacted $Br_2$ level and the other process parameters. The produced tetrabromobisphenol-A product from the process is analyzed for its tri- and tetrabromobisphenol-A content. If the tribromobisphenol-A level is too high, another trial process is constructed with a higher unreacted $Br_2$ level. The procedure is repeated until the desired product is obtained. (Note that some benefit towards reducing the tribromobisphenol-A content can also be obtained by using a higher reaction temperature.) As the chosen unreacted $Br_2$ content gets higher, care should be taken that the unreacted $Br_2$ content will not be so high that it results in the production of tribromophenol and other by-products which are not desirable from a commercial standpoint.

Measuring the unreacted $Br_2$ content of the reaction mass can be performed by the use of colorimetric techniques. A useful technique comprises the formation of an acidic (HBr) water and methanol solution. From this solution, several standard samples are prepared, to each of which is added a different and measured amount of $Br_2$. The colors of these sample solutions are then compared colorimetrically with the color of the liquid of phase of the reaction mass. A color match is indicative of the amount of $Br_2$ in the liquid phase. Colorimetric determination for unreacted $Br_2$ is quite suitable as unreacted $Br_2$ colors the sample solutions and the reaction mass in accordance with its concentration. Low concentrations give a pale yellow color; intermediate concentrations give a strong yellow color; high concentrations give an orange color; and the highest concentrations give a dark red color. Unreacted $Br_2$ concentrations in excess of 50 ppm and preferably within the range of from about 100 to about 10,000 ppm, based upon the reaction mass liquid portion, are suitable.

A more preferred amount is within the range of from about 100 to 5000 ppm, with the most preferred amount being within the range of from about 200 to 2000 ppm.

The unreacted $Br_2$ concentrations are maintained in the reaction mass so long as bisphenol-A and under-brominated species are likewise present. As can be appreciated, the unreacted $Br_2$ content diminishes as the $Br_2$ reacts, thus, the $Br_2$ feed acts to replenish the $Br_2$ in the reaction mass. Using the above-described colorimetric technique, the practitioner can monitor the unreacted $Br_2$ content of the reaction mass during the process and keep the unreacted $Br_2$ content within the chosen target range by adjusting the $Br_2$ feed, the solution feed or both. Since there will be tetrabromobisphenol-A precipitate in the reaction mass, colorimetric monitoring may require that a small stream be taken from the reactor and filtered to remove the solids before being submitted to a colorimetric technique. It may also be possible to read the intensity of the reaction mass color without filtration by the use of reflectance techniques which measure the intensity of the light reflected off of the reaction mass. In all of the colorimetric cases, the color of the liquid phase of the reaction mass is the determinative factor.

It is to be understood that techniques other than colorimetric techniques may be used in monitoring and obtaining the desired unreacted $Br_2$ level in the reaction mass. Though the particular technique used is not critical to the processes of this invention, the use of the colorimetric technique is highly preferred.

It is also to be understood that the method used to obtain the desired unreacted $Br_2$ level can be by a method other than the adjustment of the before-mentioned feeds. For example, when an oxidant is used to convert HBr to $Br_2$, the amount of $Br_2$ generated can be regulated by controlling the amount of oxidant fed to the reaction mass. The amount of unreacted $Br_2$ contributed to the reaction mass by oxidation of HBr can be substantial considering that four moles of HBr are generated for each mole of tetrabromobisphenol-A produced. Thus, when additional $Br_2$ is needed, the practitioner can use the oxidation of HBr to generate at least a part of the $Br_2$ needed to obtain the desired unreacted $Br_2$ level.

When the optional use of an oxidant is not selected, the total amount of $Br_2$ fed in the processes of this invention is at least nearly stoichiometric. Stoichiometric $Br_2$ for the ar-tetrabromination of bisphenol-A is four moles of $Br_2$ per mole of bisphenol-A. Generally, some slight excess of total $Br_2$ is used, say from about 0.1% to about 3% of stoichiometric.

When the optional oxidation of the HBr is used, the processes of this invention can obtain good results by feeding only about two moles of $Br_2$, to the reactor for every one mole of bisphenol-A fed. The other two moles of $Br_2$ that are needed are provided by the full oxidation of the co-generated HBr. If there is less than full HBr oxidation, then the amount of $Br_2$ fed to the reactor will be that amount, in sum with the $Br_2$ formed by oxidation, which will provide at least stoichiometric quantities of $Br_2$ and preferably, quantities which are in slight excess of stoichiometric as mentioned above.

Irrespective of the $Br_2$ source, the slight stoichiometric excess is desirable since it is less difficult to control the process by having excess $Br_2$ present at least during most of the reaction period. For batch processes, the excess $Br_2$ present after completion of the process can be removed by treating the reaction mass with a reducing agent such as sodium sulfite or hydrazine.

The optional oxidant material is any oxidant which is capable of oxidizing HBr to $Br_2$ in the reaction masses and under the process conditions of this invention. Preferred oxidants are those in liquid form which can facilitate their feed to the reactor. Preferred oxidants are chlorine and hydrogen peroxide.

When $Cl_2$ is the oxidant, it can be fed to the reaction mass as a gas or as a liquid. The gaseous feed is preferred. To mitigate against the formation of chlorinated bisphenol-A, it is preferred that the $Cl_2$ be fed after initiation of the $Br_2$ feed. After the initial $Br_2$ feed, $Cl_2$ can be fed contemporaneously with the $Br_2$ feed. Even with this feed sequence, some bromochlorobisphenol-A compounds will be formed. Fortunately, these bromochloro species are present in very minor amounts, say from about 50 to about 500 ppm, based on the total weight of the precipitate. The most predominate bromochloro specie will, in most cases, be chlorotribromobisphenol-A.

It is theorized that the low amount of bromochloro species is due to the fact that the bromination of the bisphenol-A to tetrabromobisphenol-A occurs rapidly. Thus, there is never a large enough concentration of under-brominated species, e.g., tribromobisphenol-A, in the reaction mass with which the $Cl_2$ can react in preference to reacting with the HBr.

When the oxidant is $H_2O_2$, safety makes it preferably that it be fed to the reaction mass in an aqueous solution containing no more than about 90 wt % $H_2O_2$. Preferred are aqueous solutions containing from about 30 to about 80 wt % $H_2O_2$. A most preferred solution is one containing from about 50 to about 70 wt % $H_2O_2$.

The $H_2O_2$ can be fed to the reaction mass at any time. For batch operation, it is preferred that the $H_2O_2$ be fed after most of the $Br_2$, say above about 50%, has been fed. For continuous operation, the $H_2O_2$ feed would most preferably occur contemporaneously with at least most of the $Br_2$ feed. Most preferably, the $H_2O_2$ feed would start after initiating the $Br_2$ feed.

The oxidants can be fed to the reaction mass separately or in some cases, along with the $Br_2$ feed. It is preferred that the $Cl_2$ be fed through the same feed conduit as is the $Br_2$ and may be fed while $Br_2$ is being fed. In distinction, the $H_2O_2$ is preferably fed as a separate feed stream.

The amount or oxidant fed is preferably that amount needed to maximize the amount of HBr oxidized without leaving a large excess of oxidant present in the reaction mass. Assuming that one mole of the oxidant chosen will oxidize two moles of HBr, the mole ratio of oxidant to bisphenol-A fed should be within the range of from about 1:1 to about 2:1. A more preferred mole ratio is from about 1.5:1 to about 1.9:1. The higher oxidant ratios are preferred when $H_2O_2$ is the oxidant, while the mid-range ratios, say 1.5–1.8:1 are preferred when $Cl_2$ is the oxidant. The reason that the lower oxidant ratios are preferred for $Cl_2$ is that there is a balance between the amount of HBr oxidized and the amount of chlorobromo species which can be tolerated. If there is no need to keep the chlorobromo species to some minimum amount, then more $Cl_2$ is permissible. Adjustments to the above ranges are necessary if the oxidant chosen does not oxidize the HBr on a one to two basis. In these cases, the ranges are adjusted in proportion to the variance in the one to two relationship.

Another important consideration in practicing the processes of this invention is the reaction mass temperature during the bromination period. It is desirable to use a relatively high temperature so that the bromination of the bisphenol-A to tetrabromobisphenol-A will be sufficiently fast to attenuate the formation of tribromobisphenol-A precipitate. However, there is a practical limit as to how high the temperature can be. For example, the practitioner would not want to use temperatures which would cause the production of unacceptable levels of unwanted by-products or the degradation of the tetrabromobisphenol-A product.

It is unusual operate a tetrabromobisphenol-A process at relatively high temperatures. This is especially so when the production of a co-product, e.g., methyl bromide, is to be minimized as it is conventional to expect that high temperatures will yield large amounts of methyl bromide. Also, the use of high temperatures is not conventional when the precipitation of the tetrabromobisphenol-A is to occur under reaction conditions soon after it is formed—such precipitation being a feature of the processes of this invention. It would be expected that high temperatures would frustrate such precipitation by increasing the solubility of the tetrabromobisphenol-A in the solvent solution and require a final cooling of or addition of water to the reaction mass to effect the desired precipitation. The processes of this invention are not so affected, nor is there required a cooling step to obtain tetrabromobisphenol-A precipitation.

Not only do the high temperatures of this invention contravene conventional tetrabromobisphenol-A thinking, but also such temperatures have been found to provide for process economy and product purity. Process economy, in part, is realized because, with higher reaction mass temperatures, the process of this invention can use cooling tower water to cool the reactor instead of having to use refrigeration which is required by the low temperature processes.

Preferred temperatures are within the range of from about 30° to about 100° C. More highly preferred temperatures are within the range of from about 50° to about 80° C. The most highly preferred temperatures are within the range of from about 50° to about 70° C. Temperatures below 30° C. can be used, but the solvent to bisphenol-A weight ratio may well need to be high, say from 8:1 to 15:1. or these ratios, temperatures of 30° to 50° C. may be suitable.

The bromination of bisphenol-A is an exothermic reaction as is the optional oxidation of HBr with $H_2O_2$. To control the reaction mass temperature, it may become necessary to remove heat from the reaction mass. Heat removal can be effected by running the reaction at reflux with the condenser facilitating the heat removal. If it is desired to operate at a temperature below the atmospheric boiling point of the reaction mixture, the reaction can be run under sub-atmospheric pressure.

Generally, the basic concepts of the processes of this invention are not appreciably affected by the process pressure. Thus, the process can be run under sub-atmospheric, atmospheric or super-atmospheric pressure.

At process initiation, it is desirable to charge the reactor with a liquid pre-reaction charge which will become a part of the reaction mass upon the commencement of the feed. The liquid charge will provide a stirrable reaction mass and act as a heat sink to moderate temperature changes in the reaction mass. The liquid charge is preferably comprised of water and the same water miscible solvent fed in the solution. It is preferred that the liquid charge be acidic, e.g., containing from 1 to 20 wt % acid such as HBr, HCl, or the like. The acid seems to promote good color in the initial tetrabromobisphenol-A produced. Further, it is preferred that the solvent be saturated with solvated tetrabromobisphenol-A. It is also preferred that the reactor be charged with seed particles of tetrabromobisphenol-A. The saturation of the solvent and the presence of the seed particles both act to enhance the precipitation or the tetrabromobisphenol-A produced during the bromination period. It is most practical to use a heel from a previously run process of this invention as the liquid charge. The tetrabromobisphenol-A seed particles can be brought over from the previous run or can be added separately. If a heel is not available, it is also possible to use a separate water and water miscible solvent feed, which are a part of the total solution feed, to form the liquid charge. In this scheme, an initial amount of water and water miscible solvent are fed to the reactor prior to the initiation of the solvated bisphenol-A portion of the solution feed. The only caveat to this scheme is that there must be apportionment of the various feeds making up the solution feed so that there will still be compliance with the various parameters which define the processes of this invention.

If the process of this invention is run as a batch process, the $Br_2$ and solution feeds are fed to a stirred reactor until they are exhausted. There is no need for a post-feed cook period of any significant length as, under the reaction conditions, the bromination of bisphenol-A to tetrabromobisphenol-A occurs quite rapidly. Also, since the water content of the reaction mass is so large and since the tetrabromobisphenol-A is so insoluble in the presence of such an amount of water, there is only a modicum of benefit in cooling the final reaction mass. The benefit of cooling resides mainly in reducing the vapor pressure of solvated gaseous bromides, e.g., methyl bromide, in the reaction mass prior to the liquid-solids separation. There also could be some slowing of the formation of these bromides. In addition, depending upon the water content of the reaction mass, cooling may allow for additional precipitation of tetrabromobisphenol-A from the reaction mass. When operating within the preferred ranges recited herein, the additional precipitation benefit may not be worth the cost associated to obtain same. Finally, depending on the separation technique used, cooling the reaction mass may make it easier to handle downstream from the reactor. Thus, if none of the above are of concern or relative value, then the reaction mass can be subjected to liquid-solids separation as soon as it can be transported to the separation equipment. If, however, cooling is desired, the cooling time will depend upon how the reaction mass is to be cooled and to what temperature it is to be cooled. In a laboratory setting, cooling times can range from about one to about thirty minutes.

Additional time may also be used between the end of the co-feed and the precipitate recovery if it is desired to add additional water to the reaction mass at the end of the co-feed to insure that even more tetrabromobisphenol-A precipitate is formed in the reaction mass. The water addition and precipitation time can be very short, say less than about thirty minutes.

Irrespective of whether or not the reaction mass is cooled or treated with more water, it is to be understood that the additional time used does not appreciably increase the total amount of tetrabromobisphenol-A produced by the process (the total amount includes that which is a precipitate and that which is solvated in the reaction mass). These additional times, therefore, are not to be considered cook times in the same way as are the cook times taught by the prior art processes.

After the recovery of the solids from the liquid, the solids are preferably washed with a solution of water and the particular water miscible solvent used in the reaction. The washing removes essentially all the mother liquor from the solids. The mother liquor contains impurities such as tribromophenol, HBr, and hydrolyzable impurities. A typical wash can be a 30 wt % methanol in water solution. The washed solids are then rewashed with deionized water to remove any remaining water miscible solvent from the first wash so as to minimize emission problems when drying the product.

When run in the continuous mode, the reactor is preferably a continuously stirred tank reactor. The reaction mass is being continuously formed and a portion thereof is being removed from the reactor during the reaction mass formation. The reactor design should be such that the average residence time in the reactor is sufficient to insure the tetrabromination of substantially all of the bisphenol-A. The terms "continuous feed" and "continuous withdrawal" are not meant to exclude interrupted feeds or withdrawals. Generally, such interruptions are of short duration and may be suitable depending upon the scale and design of the reactor. For example, since the tetrabromobisphenol-A precipitate will tend to settle near the bottom of the reactor, a withdrawal may be made and then stopped for a period of time to allow for precipitate build-up to occur prior to the next withdrawal. Such a withdrawal is to be considered continuous in the sense that the withdrawal does not await the completion of the reactor feeds as is characteristic of batch processes.

Whether the continuous withdrawal is interrupted or not, the withdrawal results in a portion of the liquid and a portion of the solids in the reaction mass to be withdrawn together. The solids portion will be predominately tetrabromobisphenol-A. This mix can be filtered, the precipitate washed, etc., as is done for the above-described batch mode case.

When using the continuous mode of operation, it is believed that it would be beneficial if the reaction mass temperature be kept fairly high as compared to the temperatures preferred for the batch mode. Preferred batch mode temperatures are from about 50° to about 65° C. For the continuous mode, the preferred temperatures are within the range of from about 55° to about 95° C., and most preferably within the range of from about 65° to about 95° C. Very good results are predicted with temperatures of from about 65° to about 75° C. By using the higher temperatures, it was found that higher purity product could be obtained.

The benefit of high temperatures on product purity is understood in view of studies which support the correlation between product purity and the relative rates of bromination and precipitation of the tribromobisphenol-A intermediate. Raising the temperature benefits both the reaction rate and the solubility of the tribromobisphenol-A in the reaction mass liquid phase and thus, promotes the obtainment of a pure product. An increase in $Br_2$ or an increase in the tribromobisphenol-A concentration in the liquid phase by reducing the liquid phase water content can also increase the bromination rate of the tribromobisphenol-A, but, they both present problems of their own. A high $Br_2$ concentration can cause the formation of undesirable by-products, while decreasing the liquid phase water content will increase the HBr content of the reaction mass and reduce tetrabromobisphenol-A yields.

It is expected that in the continuous mode of operation, the preferred reactor residence time should be within the range of from about 30 to about 150 minutes when using a stirred tank reactor and the process conditions which are preferred for that operating mode. Reactor residence time, as used here, is the reactor volume divided by the flow rate at which slurry is removed from the reactor.

The tetrabromobisphenol-A product produced by the processes of this invention can have a very high purity—say at least 98 wt % tetrabromobisphenol-A. The tribromobisphenol-A content is low--say from about 0.1 to about 2 wt %. The product quality is excellent, having an APHA color less than about 50 (80 grams of tetrabromobisphenol-A in 100 ml of acetone). Hydrolyzable bromides are also kept low, generally below about 60 ppm. The process yields are impressive, with yields within the range of from about 95 to about 99% being possible.

As can be appreciated from the foregoing, the water content of the solvent, the reaction temperature and the $Br_2$ content in the reaction mass during the bisphenol-A feed all contribute to obtaining the desired tetrabromobisphenol-A product in an efficient manner. The selection of particular values for each of these process parameters to obtain the results desired will depend on each practitioners needs and upon the equipment available. One practitioner may emphasize one benefit of using a process of this invention over other possible benefits. Thus, that practitioner may select different process parameter values than those selected by another practitioner who desires to highlight other benefit(s).

The use of the oxidation of the co-generated HBr to produce a part of the $Br_2$ needs for the processes of this invention is particularly attractive in those cases where the oxidation is more economical than the cost of providing for an equivalent amount of $Br_2$ in the feed to the reactor. The economic advantage is usually extant in those cases where the costs of feeding four moles of $Br_2$ minus the value of recovered HBr is greater than the costs of feeding two moles of $Br_2$ plus the oxidation of the HBr.

Though preferably designed to minimize the production of methyl bromide, the processes of this invention are sufficiently adaptable to be modified to produce moderate amounts of methyl bromide—say 20 lbs per 100 lbs of tetrabromobisphenol-A product. In this way, a future market need, even though greatly reduced, can be accommodated. When there is a production of methyl bromide, the total $Br_2$ requirements of the process will be those amounts needed to produce the tetrabromobisphenol-A in a high yield and to produce the targeted amount of HBr. In these cases, the $Br_2$ feed and the amount of $Br_2$ generated from oxidation must be sufficient together to meet the four $Br_2$ requirements.

While the foregoing descriptions of the oxidation of HBr generally speak of the HBr being oxidized in the reactor or reaction mass, it is within the scope of the processes of this invention to also remove co-produced HBr from the reactor and oxidize it outside of the reactor and then to send the so-produced $Br_2$ back to the reactor.

It is also within the scope of the processes of this invention to provide HBr to the reactor from a source other than the reaction in the reactor. This non-indigenous HBr can be oxidized along with the co-generated HBr to yield $Br_2$. The $Br_2$ produced from the non-indigenous HBr can then count against the total $Br_2$ needs of the process and the appropriate adjustment in the $Br_2$ feed can be made.

EXAMPLES

The following Examples illustrate principles of processes of this invention.

In each of the Examples, a pre-reaction charge or "mother liquor" was used which essentially contained water, methanol, HBr and much smaller amounts of impurities. Generally, the mother liquor contained about 30 wt % water and about 55 wt % methanol and about 8–20 wt % HBr.

The mother liquor used in Examples I–II came from TBBPA made as described in U.S. Pat. No. 4,628,124 by Mitchell and McKinnie.

In Examples III–VI, different mother liquors were used. The mother liquors used in Examples III and IV came from a series of previous experiments in which tetrabromobisphenol-A was produced by the reaction of bisphenol-A and bromine in a reaction mass containing methanol and water. These previous experiments were either not of this invention (water amounts, temperature, etc., were outside of defined parameters) or gave conflicting and inconclusive results. The mother liquor from the first experiment not of this invention was used in the second experiment and so on. The mother liquor from the last experiment provided the mother liquor for Example III.

In all Examples, unless otherwise indicated, % is to be taken as gas chromatography (GC) area percent. GC analyses were performed on a 5 Meter×0.53 mm HP-1 megabore capillary column of 2.65 micron film thickness using split injection. The column was operated from 100° C. to 300° C. with heating at 10° C. per minute. A flame ionization detector was used.

Examples I–III Illustrate the production of a high-quality tetrabromobisphenol-A product with the concomitant oxidation of co-produced HBr to $Br_2$, which $Br_2$ was used to contribute to the bromination of bisphenol-A to the desired tetrabrominated product.

Example I

A one liter round bottom flask was equipped with a mechanical stirrer, condenser, thermometer, addition funnel, heating mantle, and fitted with a ⅛ inch O.D. dip tube for feeding bromine and a ⅛ inch feed tube, which terminated in the vapor space, for feeding bisphenol-A solution. The flask was charged with 200 ml of mother liquor containing 9.5 wt % HBr and about 5.0 grams of tetrabromobisphenol-A. The added tetrabromobisphenol-A acted to saturate the mother liquor and to provide seed particles to aid in the precipitation of tetrabromobisphenol-A to be produced.

A solution comprised of 100 grams of bisphenol-A, 300 ml of methanol (2% water) and 200 ml of water was prepared. 143 grams (46 ml) of $Br_2$ was placed in a vaporizer consisting of a 250 Ml heated flask that had a nitrogen inlet and a gas outlet connected to the ⅛ inch dip tube in the reactor. The pre-reaction charge of mother liquor and tetrabromobisphenol-A was brought to a temperature of about 55° C. $Br_2$ feed was started by purging nitrogen (about 200 to 500 Ml/min) through the vaporizer and heating the liquid bromine. As soon as the pre-reactor charge took on a yellow color, the solution feed was begun by use of a peristaltic pump. The $Br_2$ feed was kept stoichiometrically ahead of the bisphenol-A feed by variation of the pumping rate, and as a result, the reaction mass had an yellow color. The feeds continued for 1 hour and 15 minutes when the $Br_2$ feed was finished. The solution feed was continued until the liquid phase of the reaction mass was colorless. The addition funnel was charged with 100 grams of aqueous $H_2O_2$ (30 wt %) and dropwise addition was initiated with the continued feed of the bisphenol-A solution.

The aqueous feed and the solution feeds were periodically adjusted to keep the liquid portion of the reaction mass a yellow color. The reaction mass temperature was kept at 60°–63° C. during the aqueous $H_2O_2$ feed. After all of the $H_2O_2$ was added the reaction mass was yellow. Continued addition of the bisphenol-A solution would turn the mass light yellow, but the deeper yellow would return upon cessation of the solution feed. During this period the reaction temperature was 58°–62° C. Finally, 20 minutes after cessation of the aqueous hydrogen peroxide feed, the bisphenol-A solution was added until the reaction mass was colorless. The reaction mass was held at a temperature of 60°–65° C. for about one-half hour and then cooled to about 55° C. The reaction mass precipitate was separated from the mother liquor by filtration and then washed with 125 ml of 20 wt % methanol in water solution. A second wash with deionized water was performed. The washed precipitate was dried and analyzed. GC analysis showed 0.64% tribromobisphenol-A and 99.3% tetrabromobisphenol-A. The mother liquor was found to contain 3.7 wt % HBr.

Example II

A one liter round bottom flask was equipped as above, except there was no addition funnel and in the line from the bromine vaporizer to the connection to the dip tube was a tee for addition of chorine gas. Mother liquor (150 grams) and 3 grams of solid tetrabromobisphenol-A were added to the flask and heated to a temperature of about 55° C. A $Br_2$ vapor and $N_2$ feed was started to the flask via the dip tube followed by the feed of a solution prepared from 80.0 grams bisphenol-A, 400 ml of methanol (2 wt % water) and 200 Ml of water. The total amount of $Br_2$ to be fed was 141 grams. After a few minutes, a slight gaseous $Cl_2$ feed was started. The liquid portion of the reaction mass was kept yellow by adjusting the bisphenol-A and $Cl_2$ feeds. All of the $Br_2$ had been fed in about 1.5 hours. The $Cl_2$ feed was increased to above 90 ml/min and was adjusted continuously to keep the liquid portion of the reaction mass yellow as bisphenol-A was fed at about 6 ml/min. All of the $Cl_2$ and bisphenol-A was fed after 2 hours. After 2 minutes from the cessation of these feeds, 2 drops of hydrazine (66 wt %) was added to destroy excess $Br_2$. The hydrazine rendered the liquid portion of the reaction mass colorless. The reaction mass was cooled to 20° C. The precipitate was collected and washed with 125 ml of 30 wt % methanol in water. A second washing with deionized water yielded a wet cake which was then oven dried at 120°–130° C. to yield 189.8 grams of product. GC analysis showed 0.79% tribromobisphenol-A, 0.01% chlorotribromobisphenol-A, 0.04% o,p-tetrabromobisphenol-A and 99.1% tetrabromobisphenol-A.

Example III

A one liter flask was equipped as in Example IV with bromine being fed as in Example IV, except that there was placed in the nitrogen feed a tee for the addition of chlorine gas. The reactor was charged with 150 Ml of a mother liquor obtained from a reaction mixture similar to Example II. This was heated to about 55° C. and addition of bromine vapor initiated. When the reaction mass took on a yellow color, the addition of a solution prepared from 90.0 grams of bisphenol-A, 450 Ml of methanol, and 180 Ml of water was started. After five minutes, the addition of 150–200 Ml per minute of chlorine gas was begun. The reaction mixture was kept at about 55° C. and was kept a yellow color by adjusting the solution flow rate. After an additional 20 minutes, chlorine flow was increase to about 250 Ml per minute and after an additional 30 minutes, chlorine flow was increased to 300 Ml per minute. 20 minutes later all bromine had been added. 47 Ml of bromine had been added. Chlorine flow rate was increased to maintain the reaction mass as a yellow color. Eight minutes later all solution had been fed, at which time chlorine addition was discontinued. After seven minutes, about 2 Ml of saturated sodium sulfite solution was added to destroy bromine. The reaction mixture was then cooled to 30° C. The solids were separated from the mother liquor by filtration and then washed on the filter with 125 Ml of 30% methanol and then 125 Ml of deionized water. The solid was oven dried leaving 209.2 grams that by GC analysis was 1.25% tribromobisphenol-A, 0.013% chlorotribromobisphenol-A, and 98.7% tetrabromobisphenol-A. The solid had an acetone color (80 grams in 100 Ml of acetone) of 20 APHA, 6 ppm ionic bromide, and 16 ppm hydrolyzable bromide. Analysis of the mother liquor showed it to contain 0.09 wt % tribromophenol, 0.21 wt % tetrabromobisphenol-A, about 3 PPM tribromobisphenol-A, and about 0.04 wt % other phenolic impurities.

The following Examples illustrate principles of processes of this invention, which processes do not feature the oxidation of HBr to provide for reactant $Br_2$.

Example IV

A one liter round bottom flask was equipped with a mechanical stirrer, condenser, thermometer, heating mantle, and fitted with a ⅛ inch O.D. dip tube for feeding bromine and a ⅛ inch feed tube, which termination in the vapor space, for feeding bisphenol-A solution. The flask was charged with 150 ml of a mother liquor and 5.0 grams of tetrabromobisphenol-A. The added tetrabromobisphenol-A acted to saturate the mother liquor and to provide seed particles to aid in the precipitation of tetrabromobisphenol-A to be produced.

A solution comprised of 59.93 grams of bisphenol-A, 360 ml of methanol (2% water) and 123 ml of water was prepared. 168.2 grams of $Br_2$ was placed in a vaporizer consisting of a 250 Ml heated flask that had a nitrogen inlet and a gas outlet connected to the ⅛ inch dip tube in the reactor. The pre-reaction charge of mother liquor and 5 grams of tetrabromobisphenol-A was brought to a temperature of about 67° C. $Br_2$ feed was started by purging nitrogen (about 200 to 500 Ml/min) through the vaporizer and heating the liquid bromine. As soon as the pre-reactor charge took on a yellow color, the solution feed was begun by use of a peristaltic pump. The $Br_2$ feed was kept stoichiometrically ahead of the bisphenol-A feed by variation of the pumping rate, and as a result, the reaction mass had an orange color. The feeds continued for 1 hour and 38 minutes when the $Br_2$ feed was finished. About 20 ml of the solution feed was left which was not added. After the solution feed was finished, the reaction mass was held for an additional 20 minutes at about 67°–69°0C. The reaction mass was colorless. The solids were collected by filtration and washed with 30% methanol in water then water and dried at a temperature of about 125° C. Gas chromatography (GC) showed the solids were comprised of 0.22% tribromobisphenol-A and: 99.8% tetrabromobisphenol-A.

Example V

Essentially, the same procedure was followed as in Example IV, except where noted. Mother liquor (150 Ml), obtained from the filtrate of Example IV, and 5 grams of tetrabromobisphenol-A were charged to the flask at the beginning. The feed solution was made from 80.0 grams bisphenol-A, 400 ml of methanol and 210 ml water. 225.4 grams of $Br_2$ were used. The solution was fed at about 6 ml/minute and the $Br_2$ was fed with a $N_2$ sweep at 200–500 ml/minute. The reaction mass was kept at a temperature of 55°–60° C. and was kept a dark yellow color by slight variation of rates of the feeds. The solution and $Br_2$ feeds were completed essentially at the same time. The flask from which the solution was fed was washed with 10 ml of methanol. The wash liquid was then fed to the reaction flask. The resultant reaction mass had a light yellow color after the wash liquid feed and five minutes from the stoppage of the solution and $Br_2$ feeds. Three drops of 63% hydrazine were added to the reaction flask to deactivate any remaining $Br_2$. The reaction mass was stirred for 1.5 hours without the addition of heat then the solids collected by filtration and washed with an aqueous 40% methanol solution then water. GC showed the solids to contain 0.02% tribromophenol, 0.84% tribromobisphenol-A and 99% tetrabromobisphenol-A.

Example VI

The same procedure was followed as in Example V, except where noted. The mother liquor (150 Ml) came from the filtrate of Example IV. Three grams of tetrabromobisphenol-A were used with the mother liquor. The solution contained 80.16 grams of bisphenol-A, 380 ml of methanol and 300 ml of water. 225.1 grams of $Br_2$ were fed. The mother liquor was heated to 55° C. and then the $Br_2$ and solution feeds were started. The reaction mass was kept yellow by adjusting the $Br_2$ feed. The two feeds were finished in about two hour, the reactor temperature being maintained at 55°–60° C. throughout the additions. The solution container was rinsed with about 10 ml of methanol which then was added to the reaction flask. The reaction mass was then light yellow. About minutes after the feeds were finished (and the methanol rinse liquid was added), 2 drops of hydrazine were added to the reaction mass. The reaction mass became colorless. The reaction mass was left to cool to room temperature and settle. A sample of the liquid portion of the reaction mass was taken. Analysis by dilution with water and extraction with methylene chloride followed by GC analysis using tetradecane as internal standard, showed that the liquid contained 0.036 wt % tribromophenol, 0.040 wt % tetrabromobisphenol-A, about 0.001 wt % tribromobisphenol-A and about 0.027 wt % other impurities, which corresponds to a yield loss of about 0.5% of theory.

The washed and dried solids recovered from the reaction mass were shown by GC to contain 1.8% of tribromobisphenol-A and 98.2% tetrabromobisphenol-A.

Example VII

A 2 liter round bottom flask was equipped as in Example IV, except the liquid bromine and a nitrogen stream (30–100 ml/min) were fed to a 6 ft length of ¼ inch teflon tubing held in boiling water to vaporize the bromine. This vaporized bromine was then fed to the ⅛ inch dip tube. A pre-reaction charge was formed by adding 18 ml of $Br_2$ over 20 minutes to a 2 L reactor which already contained 20 grams of bisphenol-A and 100 ml of methanol. The reactor contents were heated to reflux during the $Br_2$ addition and so maintained for 5 minutes after the $Br_2$ feed was completed. 100 ml of water was then added to the reactor. The resultant reactor contents comprised the pre-reaction charge.

Subsequent to the formation of the pre-reaction charge, there was added, over one hour, a co-feed comprised of 94 ml of liquid $Br_2$ and about 1400 ml of a bisphenol-A solution prepared from 130 grams of bisphenol-A, 650 ml of methanol and 950 ml of water. During the co-feed the reaction mass was a yellow to orange color and was kept at a temperature of 57°–60° C. Additional bisphenol-A solution (about 3 ml) was added after the co-feed until the reaction mass turned light yellow. The reaction mass was cooled to about 35° C. and filtered to yield a precipitate which was washed with a 30% aqueous methanol solution. Then the precipitate was washed with 250 ml of deionized water. After oven drying, the precipitate was weighed and was found to weigh 295 grams. GC analysis found 0.03% tribromophenol; 1.16% tribromobisphenol-A, 0.064% o,p-tetrabromobisphenol-A and 98.7 tetrabromobisphenol-A.

Example VIII demonstrates the use of the continuous mode for a process of this invention.

Example VIII

A 500 ml flask was equipped as in Example VII, including the bromine addition method of Example VII. There was included also a ¼ inch Teflon dip tube attached to a pump for removing reaction mixture. This pump, capable of pumping 167 Ml per minute, was attached to a timer such that it pumped reaction mixture from the flask only about 3 seconds of every 45 seconds.

The reactor was charged with 400 ml of reaction mixture from a previous run and heated to 67° C. The addition of bromine vapor was then begun. As soon as the mixture turned yellow, the addition of a solution of bisphenol-A (1000 g. bisphenol-A in 5200 ml of MeOH [3.74% water] and 1670 ml of water) was begun at a rate of about 12 ml/min. Fractions of the reaction mixture were collected in Erlenmeyer flasks that contained ½ml of 63% hydrazine. The bromine feed rate was controlled to keep the reaction mixture yellow and the reaction temperature was maintained at 69°–71° C. The reactor level was maintained at about 400 Ml by small adjustments of the rate at which the reaction mixture was pumped from the flask. After fractions were collected, they were separated from the mother liquors by filtration and the solids washed with 30% MeOH and then deionized water on the filter. Table I gives the results. Sample No. 5 was collected without added hydrazine. Analysis of it's mother liquor showed 360 ppm bromine. GC analyses of two of the mother liquors on a 5 meter HP-1 megabore capillary column using tetradecane as internal standard, are shown in Table II.

TABLE I

| Sample | Time Sample Collected, minutes | Volume of Sample Ml | % $Br_3BPA$ | % TBBPA |
|---|---|---|---|---|
| 1 | 0 to 75 | 1000 | 1.0 | 98.9 |
| 2 | 75 to 152 | 1000 | 1.0 | 98.9 |
| 3 | 152 to 306 | 2000 | 1.2 | 98.8 |
| 4 | 306 to 382 | 1000 | 1.2 | 98.7 |
| 5 | 382 to 527 | 1900 | 1.2 | 98.7 |

$Br_3BPA$ - tribromobisphenol-A
TBBPA - tetrabromobisphenol-A

TABLE II

ANALYSIS OF MOTHER LIQUOR

| GC Retention Time, min. | Compound | No. 3 Sample mother liq. | No. 5 Sample mother liq. |
|---|---|---|---|
| 5.17 | TBP | 0.040 wt % | 0.042 wt % |
| 9.76 | Unknown | 0.016 wt % | 0.017 wt % |
| 9.97 | Hydrolyzable impurity | 0.025 wt % | 0.027 wt % |
| 12.61 | DBBPA | 0.031 wt % | 0.001 wt % |
| 14.99 | $Br_3BPA$ | 0.20 wt % | 0.025 wt % |
| 17.15 | TBBPA | 0.53 wt % | 0.42 wt % |
| Total, wt % | | 0.84 wt % | 0.53 wt % |
| % Yield Loss | | 2.6 | 1.6 |

TBP - tribromophenol
DBBPA - dibromobisphenol-A
$Br_3BPA$ - tribomobisphenol-A
TBBPA - tetrabromobisphenol-A The tetrabromobisphenol-A products of this invention are of high quality—that is they contain at least about 97.5 wt % tetrabromobisphenol-A and, more preferably, at least about 98 wt % tetrabromobisphenol-A. The most highly preferred products will contain at least 98.5 wt %, with the best products containing at least 99 wt % tetrabromobisphenol-A.

It is to be understood that the processes of this invention can be run in combination with processes having process parameters not of this invention. For example, if the practitioner wished to produce an intermediate amount of methyl bromide, a process similar to the instant process can be run but with process parameters which promote the formation of methyl bromide, say for example the process could feature a low water content, e.g., 10 wt %. This process could be run for a period of time and then could be interrupted with the imposition of the parameters of this invention so as to diminish methyl bromide production. In this way, the practitioner could control the methyl bromide production within narrow production limits by combining both processes.

As can be appreciated from the above and when viewed in their broadest aspects, the processes of this invention effect the high yield production of a highly pure tetrabromobisphenol-A product by providing a reaction system in which there is directly formed a tetrabromobisphenol-A precipitate at such speed that there is insufficient opportunity for the significant precipitation of the intermediate, tribromobisphenol-A.

I claim:

1. A process for the production of tetrabromobisphenol-A, which process comprises:
   a. feeding, to a reactor, a solution comprised of bisphenol-A, water and a water miscible solvent to at least partially form a reaction mass having a liquid phase containing from above about 15 to about 65 wt % water, the wt % being based upon the amount of water and water miscible solvent in the liquid phase;
   b. substantially throughout the feed in (a), providing for the presence of from about 100 to about 10,000 ppm unreacted $Br_2$ in the reaction mass to yield, substantially throughout the feed in (a), a precipitate containing at least about 97.5 wt % tetrabromobisphenol-A; and
   c. substantially throughout the feed in (a), having a reaction mass temperature which is within the range of from about 30° to about 100° C.

2. The process of claim 1 wherein the water miscible solvent is methanol or ethanol.

3. The process of claim 1 wherein the miscible solvent is methanol.

4. The process of claim 1 wherein the reaction mass contains from about 25 to about 65 wt % water.

5. The process of claim 1 wherein the reaction mass contains from about 30 to about 45 wt % water.

6. The process of claim 1 wherein the reaction mass contains from about 100 to 5,000 ppm unreacted $Br_2$.

7. The process of claim 1 wherein the reaction mass contains from about 200 to about 2,000 ppm unreacted $Br_2$.

8. The process of claim 1 wherein the reaction mass temperature is within the range of from about 50° to about 80° C.

9. The process of claim 1 wherein HBr in the reaction mass during (a) is oxidized to $Br_2$ during (a).

10. The process of claim 9 wherein the oxidant is $H_2O_2$.

11. The process of claim 1 wherein tetrabromobisphenol-A is removed from the reactor during (a).

12. The process of claim 1 wherein the precipitate contains at least about 98.5 wt % tetrabromobisphenol-A.

13. The process of claim 1 wherein the liquid phase of the reaction mass, at process initiation, is saturated with tetrabromobisphenol-A.

14. The process of claim 1 wherein the liquid phase of the reaction mass, at process initiation, contains from about 1 to about 20 wt % acid.

15. The process of claim 1 wherein the liquid phase of the reaction mass, at process initiation, contains from about 1 to about 20 wt % acid and is saturated with tetrabromobisphenol-A.

16. The process of claim 1 wherein the process is run in the batch mode.

17. The process of claim 1 wherein the process is run in the continuous mode.

18. The process of claim 9 wherein less than all of the HBr present during (b) is oxidized to $Br_2$.

19. A process for the production of tetrabromobisphenol-A, which process comprises:
   a. providing a reaction mass liquid phase having (i) a presence of from about 100 to about 10,000 ppm unreacted $Br_2$, (ii) from about 15 to 65 wt % water and (iii) a water miscible solvent for bisphenol-A, the wt % being based on the amount of water and water miscible solvent in the liquid phase;
   b. feeding, to the reaction mass, a solution comprised of bisphenol-A, water and a water miscible solvent to contemporaneously form a precipitate during substantially all of the feeding period of the solution, which precipitate contains at least about 97.5 wt % tetrabromobisphenol-A;
   c. during the solution feeding period in (b), adding $Br_2$ to the reaction mass to maintain, during substantially all of the solution feeding period, the presence of from about 100 to about 10,000 ppm unreacted $Br_2$ in the liquid phase of the reaction mass; and
   d. during substantially all of the solution feeding period, maintaining the reaction mass temperature within the range of from about 30° to about 100° C.

20. The process of claim 19 wherein the liquid phase of the reaction mass, at process initiation, is saturated with tetrabromobisphenol-A.

21. The process of claim 19 wherein the liquid phase of the reaction mass, at process initiation, contains from about 1 to about 20 wt % acid.

22. The process of claim 19 wherein the liquid phase of the reaction mass, at process initiation, contains from about 1 to about 20 wt % acid and is saturated with tetrabromobisphenol-A.

23. The process of claim 19 wherein the solvent is methanol or ethanol.

24. The process of claim 19 wherein the process is run in the batch mode.

25. The process of claim 19 wherein the process is run in the continuous mode.

26. The process of claim 19 wherein HBr, which is in the reaction mass during the solution feed period in (b), is oxidized to $Br_2$ during (b).

27. The process of claim 26 wherein less than all of the HBr present during (b) is oxidized to $Br_2$.

28. The process of claim 19 wherein the reaction mass temperature is within the range of from about 50° to about 800° C.

29. The process of claim 19 wherein the reaction mass contains from about 100 to about 5,000 ppm unreacted $Br^2$.

30. The process of claim 19 wherein the reaction mass contains from about 200 to about 2,000 ppm unreacted $Br_2$.

* * * * *

UNITED STATES PATENT AND TRADEMARK OFFICE
CERTIFICATE OF CORRECTION

PATENT NO. : 5,847,232
DATED : Dec. 8, 1998
INVENTOR(S) : Bonnie G. McKinnie

It is certified that error appears in the above-indentified patent and that said Letters Patent is hereby corrected as shown below:

Cover Page

Item [56]               References Cited, under

Foreign Patent Documents
                              insert the following:
                              9611227   4/1996   WIPO.

Signed and Sealed this

Twenty-third Day of March, 1999

Attest:

Q. TODD DICKINSON

Attesting Officer          Acting Commissioner of Patents and Trademarks